United States Patent [19]

Kumobayashi et al.

[11] 4,144,257
[45] Mar. 13, 1979

[54] PROCESS FOR PREPARING DERIVATIVES OF CONJUGATED DIENE DIMERS

[75] Inventors: Hidenori Kumobayashi, Chigasaki; Susumu Akutagawa; Akira Komatsu, both of Tokyo, all of Japan

[73] Assignee: Takasago Perfumery Co., Ltd., Tokyo, Japan

[21] Appl. No.: 709,982

[22] Filed: Jul. 30, 1976

Related U.S. Application Data

[63] Continuation of Ser. No. 515,754, Oct. 17, 1974, abandoned, which is a continuation-in-part of Ser. No. 404,051, Oct. 5, 1973, abandoned.

[51] Int. Cl.$^2$ ............... C07C 121/30; C11C 3/00; C07C 47/20; C07C 49/20
[52] U.S. Cl. ............ 260/410.9 R; 260/465.9; 260/593 R; 260/601 R; 260/669 P
[58] Field of Search ............ 260/410.9 R, 669 P, 260/465.3, 465.9, 597 R, 604 R, 601 R, 593 R, 410.9 M

[56] References Cited

U.S. PATENT DOCUMENTS

| | | | |
|---|---|---|---|
| 3,390,195 | 6/1968 | Chappell et al. | 260/669 P |
| 3,417,130 | 12/1968 | Pruett et al. | 260/593 R X |
| 3,493,590 | 2/1970 | Chabardes | 260/419.9 R |
| 3,660,440 | 5/1972 | Wilke et al. | 260/410.9 R |
| 3,676,470 | 7/1972 | Takahashi et al. | 260/465.9 |
| 3,755,386 | 8/1973 | Wilke et al. | 260/410.9 R |

FOREIGN PATENT DOCUMENTS 1014541 12/1965 United Kingdom.

*Primary Examiner*—Joseph Paul Brust
*Attorney, Agent, or Firm*—Sughrue, Rothwell, Mion, Zinn and Macpeak

[57] ABSTRACT

A process for preparing derivatives of isoprene dimers, which are useful as materials for producing perfumes, pharmaceuticals and industrial chemicals, comprising catalytically reacting isoprene with an active methyl-containing compound, such as methacrylonitrile, using bis-π-allyl nickel or bis-cyclooctadiene nickel as a catalyst and triphenyl phosphine, triphenyl phosphite, tributyl arsenic or tricyclohexyl phosphine as a ligand and a tertiaryamine compound as a solvent.

12 Claims, No Drawings

PROCESS FOR PREPARING DERIVATIVES OF CONJUGATED DIENE DIMERS

CROSS-REFERENCE TO RELATED APPLICATIONS

This application is a continuation application of Ser. No. 515,754, filed Oct. 17, 1974 now abandoned and in turn a continuation-in part application of Ser. No. 404,051, filed Oct. 5, 1973, also now abandoned.

BACKGROUND OF THE INVENTION

1. Field of the Invention

This invention relates to a process for preparing derivatives of isoprene dimers, and, more specifically, to a process for preparing derivatives of isoprene dimers by reacting isoprene in the dimerized form with active methyl-containing compounds.

2. Description of the Prior Art

Many methods have been reported for reacting conjugated dienes using metal complexes as a catalyst, but there has been no prior report in which oxygen-containing, nitrogen-containing compounds are directly produced from isoprene and active methyl-containing compounds.

It has now been found that the use of a special nickel complex catalyst makes it possible in one step to produce natural terpene type compounds (in which isoprene is bonded at the 1,4-carbons) useful as intermediates for perfumes, medicinals and other industrial chemicals by reacting isoprene and acitve methyl-containing compounds.

SUMMARY OF THE INVENTION

According to this invention, there is provided a process for preparing derivatives of isoprene dimers expressed by the following formula

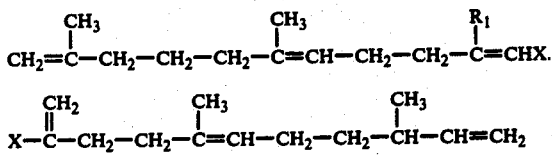

Wherein $R_1$ is a hydrogen atom or a methyl group, and

X is a cyano group, an aldehyde group, an acetyl group: a carbomethoxy group, a carboethoxy group or a phenyl group, which comprises catalytically reacting isoprene with a compound containing an active methyl group which is expressed by the general formula

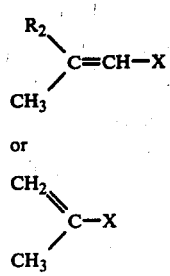

wherein $R_2$ is a hydrogen atom or a methyl group, and X is as defined above, in the presence of a nickel complex catalyst expressed by the general formula $$Ni^o \leftarrow L$$

wherein $Ni^o$ represents bis-$\pi$-allyl nickel or bis-cyclooctadiene nickel and L represents a ligand consisting of one or more of $P(R'')_3$, $As(R'')_3$, $Sb(R'')_3$, or $P(OR'')_3$, R'' being an alkyl group, a cycloalkyl group or a phenyl group, using a tertiary amine compound such as pyridine, diethylaniline and triethylamine, as a solvent.

This reaction is a novel reaction, and by utilizing this reaction, a number of natural terpene type compounds (isoprene is bonded at 1,4-carbon) including perfumes and medicinals can be synthesized. Accordingly, this reaction has a wide range of utility.

DETAILED DESCRIPTION OF THE INVENTION

In the reaction with isoprene, the second reactant, an active methyl-containing compound, is expressed by the general formula (I) or (II) below

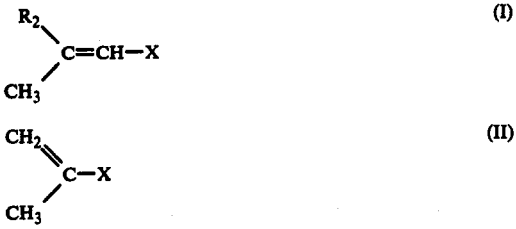

wherein $R_2$ is a hydrogen atom or a methyl group, and X is a cyano group, an aldehyde group, an acetyl group, a carbomethoxy group, a carboethoxy group or a phenyl group. Examples of compound of the general formula (I) are mesityl oxide, ethyl crotonate, ethyl $\beta,\beta$-dimethylacrylate, and crotonaldehyde. Examples of compounds of the general formula (II) are methacrylonitrile, methyl methacrylate, aceto isopropene, and $\alpha$-methyl styrene.

The use of a nickel complex catalyst is essential in the process of this invention. The nickel complex catalyst is expressed by the following general formula (III)

$$Ni^o \leftarrow L \qquad (III)$$

wherein $Ni^o$ represents bis-$\pi$-allyl nickel or bis-cyclooctadiene nickel and L represents a ligand consisting of one or more of $P(R'')_3$, $As(R'')_3$, $Sb(R'')_3$, or $P(OR'')_3$, with R'' being an alkyl group, a cycloalkyl group or a phenyl group.

These nickel complex catalysts can be prepared using known methods, for example, the methods disclosed by G. Wilke, *Angewandte Chemie*, 72, 581–582 (1960); 73, 755–756 (1961). The complexes can also be prepared by mixing a nickel complex such as bis-$\pi$-allyl-nickel, bis-cyclooctadiene-nickel and a ligand.

In the reaction of the present invention, in using a tertiary amine compound, the by-production of isoprene oligomer is reduced, whereby the yield of the desired derivative increases. Suitable examples of a tertiary amine compound which can be used include, pyridine, diethylaniline, triethylamine and the like.

Examples of the synthesis of these nickel complex catalysts are set forth hereinbelow.

(I) Preparation of bis-cyclooctadiene nickel 20 m moles of nickel acetylacetonate was suspended in 20 ml of n-hexane and 20 ml of 1,5-cyclooctadiene, and an n-hexane solution containing 100 m moles of diethyl aluminum ethoxide [$(C_2H_5)_2AlOC_2H_5$] was added dropwise thereto at a temperature of $-5°$ to $-10°$ C. The resulting yellow colored crystals were filtered out and then recrystallized from benzene. Thus, bis-cyclooctadiene nickel was obtained.

(II) Preparation of bis-$\pi$-allyl nickel 100 m moles of allyl magnesium chloride which was prepared in diethyl ether was slowly added to 20 m moles of anhydrous nickel bromide which was suspended in diethyl ether, at a temperature of $-10°$ to $-20°$ C. The resulting yellow colored solution was filtered out to remove the diethyl ether. Thus, 10 m moles of yellow colored crystals of bis-$\pi$-allyl nickel was obtained.

The process of this invention is carried out by reacting a mixture of isoprene, the active methyl-containing compound, the nickel complex, and the ligand in the solvent of the tertiary amine compound. The ratio of isoprene to the active methyl-containing compound which can be employed is basically a stoichiometric amount but, preferably the amount of isoprene employed is in an excess amount of 10 to 20% from the standpoint of economics. The preferred amount of the catalyst is 1 to 5 mol% based on the weight of isoprene and the mol or ratio of the nickel complex to the ligand is 1:1. The solvent of a tertiary compound is used in an amount of 10 to 200% by volume, preferably 100 to 150% by volume based on the volume of isoprene.

The reaction is performed generally at a temperature of 50° to 150° C., preferably 80° to 100° C., for 2 to 14 hours in an inert gas atmosphere such as an argon or a nitrogen gas atmosphere, with nitrogen being preferred, using a pressure vessel. The preferred reaction time is 10 to 14 hours. The reaction is conducted in a pressure vessel under autogenous pressures of the isoprene. At temperatures near the lower limit of the reaction temperature range (about 50° C.), the pressure is generally about 2 Kg/cm$^2$, and at temperatures near the upper limit of the reaction temperature (about 150° C.), the pressure is generally about 11 Kg/cm$^2$. A preferred pressure range is 5 to 7 Kg/cm$^2$. Under these conditions, the reaction proceeds advantageously to provide the product desired.

When a mixture of the starting compounds, the nickel (o) complex and the ligand is reacted, a nickel complex of the formula (III) is first formed in the reaction system and acts as a catalyst.

The compound obtained is expressed by the general formula

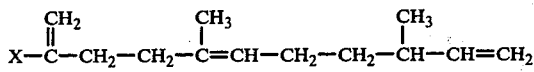

where the active methyl-cotaining compound expressed by the formula (I) is used as a reactant, and by the general formula

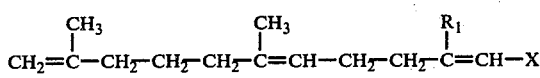

where the active methyl-containing compound expressed by the general formula (II) is used. In these formulae, $R_1$ and X are the same as defined above. These compounds are very useful as materials for perfumes (e.g., the product per se can be used as a perfume), pharmaceuticals, and industrial chemicals.

The following Examples are given to illustrate the present invention in greater detail. Unless otherwise indicated all parts and percentages are by weight.

EXAMPLE 1

A 200 ml pressure vessel was charged with 1.6 g of triphenyl phosphine, and after purging the vessel with nitrogen, 100 ml of isoprene 1 g of bis-cyclooctadienyl nickel and 50 ml of pyridine was added with sufficient stirring. The mixture was stirred for 10 minutes, and 40 g of mesityl oxide was added, after which the vessel was sealed. The reaction was performed at 80° C. for 14 hours. Then, the reaction mixture was decomposed with dilute hydrochloric acid (30 ml 6 N). And further, triplicate extraction processes were conducted using 100 ml of diethyl ether, the resulting ether-extract was washed with a 3% sodium bicarbonate solution one time and then the product thus obtained was washed three times with water. To the resulting ether-extracted solution, anhydrous sodium sulfate was added for drying. The dried ether-extracted solution was removed into a Claisen flask and vacuum distillation was conducted to afford 50 g of a fraction boiling at 110° to 120° C./2 mmHg. This fraction was analyzed using gas-chromatography, infrared absorption spectral analysis, nuclear magnetic resonance spectral and mass spectral analysis, and found to contain 80% of 4,8,12-trimethyl-3,7,12-tridecatrien-2-one.

Elemental analysis for $C_{16}H_{28}O_2$—Calculated (%): C 82, H 11.1. Found (%): C 81.52, H 11.28.

EXAMPLE 2

A 200 ml pressure vessel was charged with 1.7 g of triphenyl phosphite, and in a stream of nitrogen, 100 ml of isoprene, 1.5 g of bis-$\pi$-allyl nickel and 20 ml of diethyl aniline was added. The mixture was then stirred for 10 minutes, and 45 g of ethyl crotonate was added, after which the vessel was sealed. The reaction was performed at 80° C. for 14 hours. After the reaction, the reaction mixture was decomposed with dilute hydrochloric acid, subjected to the work up procedures described in Example 1, and distilled to afford 60 g of a fraction boiling at 130°–135° C./5 mmHg. The fraction was analyzed using gas-chromatography, infrared absorption spectal analysis, nuclear magnetic resonance spectral analysis and mass spectral analysis, and found to contain 75% of 1-carboethoxy-6,10-dimethyl-1,5,10-undecatrienoate.

Elemental analysis for $C_{16}H_{26}O_2$—Calculated (%): C 76.7, H 10.4. Found (%): C 76.35, H 10.48.

EXAMPLE 3

A 200 ml pressure vessel was charged with 1.5 g of bis-cyclooctadienyl nickel, 2 g of triphenylphosphite, 100 ml of isoprene and 100 ml of pyridine in a stream of nitrogen. 51 g of ethyl $\beta,\beta$-dimethylacrylate was added, after which the vessel was sealed. The reaction was performed at 80° C. for 10 hours. After the reaction, the reaction mixture was decomposed with dilute hydrochloric acid, subjected to the work up procedures described in Example 1, and distilled to afford 65 g of a fraction boiling at 140° to 150° C./5 mmHg. This fraction was analyzed using gas-chromatography, infrared absorption spectral analysis, nuclear magnetic resonance spectral analysis and mass spectral analysis, and found to contain 75% of 1-carboethoxy-2,6,10-trimethyl-1,5,10-undecatrienoate.

Elemental analysis for $C_{17}H_{28}O_2$—Calculated (%): C 78, H 10.22. Found (%): C 78.5, H 10.32.

EXAMPLE 4

A 200 ml pressure vessel was charged with 2 g of bis-cyclooctadienyl nickel and 3 g of triphenyl phosphine in a stream of nitrogen, and 100 ml of isoprene and 100 ml of triethyl amine was added. 47 g of α-methyl styrene was added, after which the vessel was sealed. The reaction was performed at 80° C. for 13 to 14 hours. After the reaction, the reaction mixture was decomposed with dilute hydrochloric acid, subjected to the work up procedures described in Example 1, and distilled to afford 30 g of a fraction boiling at 150° to 155° C./5 mmHg. This fraction was analyzed using gas-chromatography, infrared absorption spectral analysis, nuclear magnetic resonance spectral analysis and mass spectral analysis, and found to contain 85% of 2-phenyl-5,9-dimethyl-1,5,10-undecatriene.

Elemental analysis for $C_{19}H_{26}$—Calculated (%): C 89.8, H 10.2. Found (%): C 89.0, H 10.03.

EXAMPLE 5

A pressure vessel was charged with 50 ml of isoprene, 1.56 g of bis-π-allyl nickel and 1.3 g of triphenyl phosphine in a nitrogen atmosphere, and the mixture was stirred for 10 minutes. Then, 16.7 g of methacrylonitrile and 100 ml of pyridine was added, and the reaction was performed at 60° C. for 13 hours. After the reaction, the reaction mixture was decomposed with dilute hydrochloric acid, extracted with diethyl ether, and concentrated and distilled to afford 15 g of a fraction boiling at 90° to 95° C./0.1 mmHg. This fraction was analyzed using gas-chromatography, infrared absorption spectral analysis, nuclear magnetic resonance spectral analysis, and mass spectral analysis, and found to contain 60% of 2-cyano-5,9-dimethylundeca-1,5,10-triene.

Elemental analysis for $C_{14}H_{21}N$—Calculated (%): C 82.7, H 10.41, N 6.89. Found (%): C 82.73, H 10.6, N 6.52.

EXAMPLE 6

A 200 ml of pressure vessel was charged with 1.5 g of bis-π-allyl nickel and 1.5 g of tributyl arsenic in a stream of nitrogen, and 100 ml of isoprene and 150 ml of triethylamine was added. 28 g of crotonaldehyde was further added, after which the vessel was sealed. The reaction was performed at 80° C. for 14 hours. After the reaction, the reaction mixture was decomposed with dilute hydrochloric acid, subjected to the work up procedures described in Example 1, and then distilled to afford 30 g of a fraction boiling at 100° to 115° C./5 mmHg. This fraction was analyzed using gas-chromatography, infrared absorption spectral analysis, nuclear magnetic resonance spectral analysis and mass spectral analysis, and found to contain 95% of 6,10-dimethyl-1,5,10-undecatrien-1-aldehyde.

Elemental analysis for $C_{14}H_{20}O$—Calculated (%): C 82.3, H 9.83. Found (%): C 81.8, H 10.1.

EXAMPLE 7

A pressure vessel was charged with 50 ml of isoprene and 50 ml of diethylaniline in a nitrogen atmosphere, and 1.37 g of bis-cyclooctadiene nickel and 1.3 g of triphenyl phosphine were added, followed by further addition of 25 g of methyl methacrylate. The reaction was performed at 50° C. for 14 hours, and treated in the same manner as described in Example 5 to afford 25 g of a fraction having a boiling point of 100° to 105° C./0.1 mmHg. This fraction was analyzed using gas-chromatography, infrared absorption spectral analysis, nuclear magnetic resonance spectral analysis and mass spectral analysis, and found to contain 70% of 2-carbomethoxy-5,9-dimethylundeca-1,5,10-triene.

Elemental analysis for $C_{15}H_{24}O_2$—Calculated (%): C 76.22, H 10.24. Found (%): C 76.30, H 10.04.

EXAMPLE 8

A pressure vessel was charged with 50 ml of isoprene in a nitrogen atmosphere, and 1.35 g of bis-cyclooctadienyl nickel and 1.4 g of tricyclohexyl phosphine were added. The mixture was then stirred for 10 minutes, and 21 g of aceto isopropene and 50 ml of pyridine was added finally. The reaction was performed at 60° C. for 14 hours. After the reaction, the reaction mixture was treated in the same manner as described in Example 5 to afford 20 g of a fraction having a boiling point of 80° to 90° C./0.1 mmHg. The fraction was analyzed using gas-chromatography, infrared absorption spectral analysis, nuclear magnetic resonance spectral analysis and mass spectral analysis, and found to contain 50% of 2-acethyl-5,9-dimethylundeca-1,5,10-triene.

Elemental analysis for $C_{15}H_{24}O$—Calculated (%): C 81.76, H 10.98. Found (%): C 81.1, H 10.92.

While the invention has been described in detail and with reference to specific embodiments thereof, it will be apparent to one skilled in the art that various changes and modifications can be made therein without departing from the spirit and scope thereof.

What is claimed is:

1. A process for preparing derivatives of isoprene dimers having the following formula

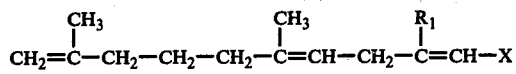

Wherein $R_1$ is a hydrogen atom or a methyl group and X is an aldehyde group, an acetyl group, a carbomethoxy group, or a carboethoxy group, which comprises catalytically reacting in the presence of an inert gas atmosphere and at a temperature of 50° to 150° C. for 2 to 14 hours isoprene with a compound containing an active methyl group and having the general formula

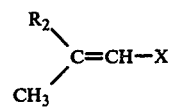

wherein $R_2$ is a hydrogen atom or a methyl group and X is as defined above, in the presence of 1 to 5 mol% based on the weight of the conjugated diene compound of a nickel complex catalyst having the general formula

wherein $Ni^0$ represents bis-π-allyl nickel complex or bis-cyclooctadiene nickel complex and L represents a ligand consisting of one or more of $P(R'')_3$, $As(R'')_3$, $Sb(R'')_3$, or $P(OR'')_3$, $R''$ being an alkyl group, a cycloalkyl group or a phenyl group, the molar ratio of said nickel complex to said ligand being about 1:1, in a tertiary amine selected from the group consisting of pyridine, diethylaniline and triethylamine as a solvent, said solvent being present in an amount of about 10 to 200% by volume based on volume of isoprene.

2. The process of claim 1, wherein the reaction temperature is 80° to 100° C.

3. The process of claim 1, wherein the reaction time is 10 to 14 hours.

4. The process of claim 1, wherein the active methyl-containing compound is selected from the group consisting of mesityl oxide, ethyl crotonate, ethyl β,β-dimethylacrylate, crotonaldehyde.

5. The process of claim 1, wherein the nickel complex catalyst is formed in situ from a bis-π-allyl nickel complex or a bis-cyclooctadiene nickel complex and a ligand consisting of one or more of said P(R")$_3$, As(R")$_3$, Sb(R")$_3$, or P(OR")$_3$ wherein R" is as defined in claim 1.

6. The process of claim 4, wherein the ligand is triphenyl phosphine, triphenyl phosphite, tributyl arsenic or tricyclohexyl phosphine.

7. A process for preparing derivatives of isoprene dimers having the following formula

wherein X is a cyano group, an acetyl group, a carbomethoxy group, a carboethoxy group or a phenyl group, which comprises catalytically reacting in the presence of an inert gas atmosphere and at a temperature of 50° to 150° C. for 2 to 14 hours isoprene with a compound containing an active methyl group and having the general formula

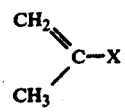

wherein X is as defined above, in the presence of 1 to 5 mol% based on the weight of the conjugated diene compound of a nickel complex catalyst having the general formula

wherein Ni° represents bis-π-allyl nickel complex or bis-cyclooctadiene nickel complex and L represents a ligand consisting of one or more of P(R")$_3$, As(R")$_3$, Sb(R")$_3$, and P(OR")$_3$, R" being an alkyl group, a cycloalkyl group or a phenyl group, the molar ratio of said nickel complex to said ligand being about 1:1, in a tertiary amine selected from the group consisting of pyridine, diethylaniline, and triethylamine as a solvent, said solvent being present in an amount of about 10 to 200% by volume based on volume of isoprene.

8. The process of claim 7, wherein the reaction temperature is 80° to 100° C.

9. The process of claim 7, wherein the reaction time is 10 to 14 hours.

10. The process of claim 7, wherein the active methyl-containing compound is selected from the group consisting of methacrylonitrile, methyl methacrylate, methyl isopropenyl ketone, and α-methyl styrene.

11. The process of claim 7, wherein the nickel complex catalyst is formed in situ from a bis-π-allyl nickel complex or a bis-cyclooctadiene nickel complex and a ligand consisting of one or more of said P(R")$_3$, As(R")$_3$, Sb(R")$_3$, or P(OR")$_3$ wherein R" is as defined in claim 7.

12. The process of claim 11, wherein the ligand is triphenyl phosphine, triphenyl phosphite, tributyl arsenic or tricyclohexyl prophine.

* * * * *